United States Patent [19]

Killion et al.

[11] Patent Number: 5,113,967
[45] Date of Patent: May 19, 1992

[54] AUDIBILITY EARPLUG

[75] Inventors: Mead C. Killion, Elk Grove Village; Jonathan K. Stewart, Bensenville, both of Ill.; Robert Falco; Elliott H. Berger, both of Indianapolis, Ind.

[73] Assignee: Etymotic Research, Inc., Elk Grove Village, Ill.

[21] Appl. No.: 519,855

[22] Filed: May 7, 1990

[51] Int. Cl.⁵ .................................... A61B 7/02
[52] U.S. Cl. ......................... 181/132; 181/135
[58] Field of Search ............ 181/135, 137; 128/864, 128/868

[56] References Cited

U.S. PATENT DOCUMENTS 4,540,063 9/1985 Ochi et al. ..................... 181/135
4,807,612 2/1989 Carlson ........................... 128/868
4,852,683 8/1989 Killion ........................ 181/135 X Primary Examiner—Russell E. Adams
Assistant Examiner—Jae N. Noh
Attorney, Agent, or Firm—McAndrews, Held & Malloy, Ltd.

[57] ABSTRACT

An earplug uses damping to render unimportant a Helmholtz resonance between the acoustic mass intrinsic to a sound channel thereof and the compliance of air in the earcanal, in combination with a readily manufacturable external structure coupled to the sound channel to increase response characteristics at higher frequencies in a predictable and well controlled manner in order to provide a highly desireable uniform frequency response.

2 Claims, 4 Drawing Sheets

AUDIBILITY EARPLUG

BACKGROUND OF THE INVENTION

1. Field of the Invention.

This invention relates to improved devices for providing hearing protection from exposure to sounds that are intense enough to risk hearing damage or discomfort.

2. Background of the Prior Art

It is well documented that repeated or prolonged exposure to sounds of sufficiently high sound pressure level (SPL) will cause temporary or permanent hearing loss. Earplugs and earmuffs suitable for preventing hearing loss have been widely available, but until recently have all been characterized by a common limitation in that they provide much greater attenuation at high frequencies than at low frequencies and/or provide excessive attenuation at high frequencies. The result was that the user who wanted or needed to hear clearly was prevented from doing so.

More recently, high fidelity earplugs suitable for use with custom earmolds have been introduced by Etymotic Research, Inc., licensed under U.S. Pat. No. 4,807,612 issued Feb. 28, 1989 to Elmer Carlson. These provide a uniform attenuation of approximately 15 dB across the entire audible frequency band, from 20 Hz to 16 kHz, as confirmed by applicants own measurements and, more recently, measurements performed on 16 subjects in the diffuse-field test chamber in the Indianapolis facilities of E-A-R company. These have been well accepted by symphony musicians, rock musicians, and others who need some hearing protection but also need to hear clearly while wearing earplugs.

While giving superb acoustical performance, the Carlson earplug has several limitations:

1. The diaphragm compliance element required by the Carlson earplug is difficult (and thus relatively costly) to manufacture to the tight compliance tolerance required for proper operation.

2. The Carlson earplug requires a precise and relatively large diameter internal sound channel in the accompanying custom earmold in order that the Helmholtz resonance between the acoustic mass intrinsic to that internal sound channel and the compliance of air in the earcanal have the proper frequency. A consequent limitation to the Carlson earplug has been the necessity of obtaining a specially manufactured custom earmold for each ear, where it has been found that the earmold manufacturer must individually measure and "tune" the internal sound channel using a special meter manufactured by Etymotic Research in order to provide the correct value of acoustic mass required for proper operation.

3. As a result of limitations 1 and 2, the Carlson earplug has been deliverable to the end user only at a relatively high overall cost, typically $100 to $125 per pair to the end user. This cost and inconvenience may be of relatively little concern to a professional musician, but they have hampered the widespread application of the Carlson earplug to recreational and industrial users.

The need for an inexpensive improved audibility earplug has become clearer as the ready availability of the Carlson earplug has generated further thinking and discussion. A common problem in industry has been that workers do not wear the mandatory ear protection properly, sometimes complaining that it is difficult to hear properly with standard earplugs in place. Studies reported by Elliott Berger of E-A-R corporation have shown average values of Noise Reduction Rating (NRR) of 2 to 10 dB when NRR is measured in the real-world environment as workers are actually using their earplugs, even on earplugs with rated NRR values of 20 to 30 dB based on laboratory attenuation measurements. Applicants interpret this as an indication that some workers learn how to compromise the performance of hearing protectors (by inserting them only half way, for example) when the attenuation they provide is excessive for the situation. The problem with the half-inserted or partially sealed earplugs is that they still provide excessive attenuation at high frequencies even though the attenuation at low frequencies is reduced, creating a muffled sound that makes it difficult to understand speech or monitor machinery for proper operation. When the workers have a mild to moderate hearing loss, the attenuation of the hearing protector is added to the "internal attenuation" they already endure due to their hearing loss, further increasing their resistance to hearing protection. The most recent estimates are that whereas some two-thirds of factory workers work in environments where the noise level exceeds 85 dB(A) daily weighted average, and thus some hearing protection is needed to prevent hearing loss, three-fourths of those workers need less than 10 dB of protection. In the absence of a readily available improved-audibility earplug, it appears that many workers compromise the performance of their earplugs, or some simply refuse to wear ear protection, risking further hearing loss.

Subsequent to the Carlson earplug, a lower-cost earplug with improved audibility was described in U.S. Pat. No. 4,852,683, issued Aug. 1, 1989 to Mead C. Killion, one of the present applicants. The disclosure thereof is incorporated herein by reference. That patent application describes in greater detail both the prior art and the Carlson earplug. The Killion earplug solved the principal limitation of the Carlson earplug by using damping to render the Helmholtz resonance unimportant, adding an external structure coupled to the sound channel to increase the response characteristics at higher frequencies.

In a preferred "loop-tube" version, the Killion earplug used an external plastic tube formed into a "loop" shape to form a quarter-wave resonance and, by using an appropriately larger diameter in the external loop tube than in the internal sound channel, obtained desirable "horn" action to further improve the high frequency characteristics of the resulting earplug. Good performance has been obtained with this external loop tube, plus an adapter tube containing the damping element, coupled to slow-recovery foam eartips (Reissue U.S. Patent No. 29,487 Reissued Dec. 6, 1977 to Ross Gardner, Jr.) that have internal 0.076" i.d. "#13" vinyl sound tubes. These foam eartips are readily available from Etymotic Research under the designation "ER-3-14 eartips" or from E-A-R corporation under the designation "EARLINKS." Good performance has also been obtained using three-flanged molded eartips available from E-A-R corporation under the designation "UltraFit," when the latter have been specially molded to include an internal 0.076" i.d. sound channel. Applicants' company Etymotic Research has assembled and sold improved audibility earplugs of the latter construction on a limited basis with good results.

SUMMARY OF THE INVENTION

This invention was evolved with the general object of providing earplugs having acoustical performance characteristics which match the requirements of wearers of the earplugs while being of compact size and comfortable to wear and while being readily and economically manufacturable.

Important aspects of the invention relate to the discovery and recognition of problems with prior constructions and to analyses of areas in which improvements might be made as well as features which are desirably retained. For example, while excellent results were obtained with the aforementioned loop-tube version of the Killion earplug, it was found that in our production thereof, an unexpected cost limitation was realized because the loop tubes were difficult to form on a production basis while maintaining an accurate internal diameter. In particular, the loop tubes tended to flatten in the bend area, compromising the overall acoustic performance at the higher frequencies, so the overall reject rate was high when simple and inexpensive forming techniques were used.

A further limitation of the loop-tube version of the Killion earplug for some applications was its appearance, which was judged by some to be cosmetically unattractive for sale at "rock" music concerts and the like, one of its important potential applications.

In accordance with the invention, an earplug is provided in which an eartip or the like is arranged for positioning with at least an inner end portion thereof in an earcanal to define a first sound passage extending from an inner end within the ear canal to an opposite outer end, and in which a second sound passage is formed by a structure which is preferably external to the ear canal, the second sound passage having an inner end coupled to the outer end of the first passage and having an opposite sound-receiving outer end. An important feature is that the second passage includes a portion folded back on itself, the second sound passage being operative to enhance the acoustical response characteristics of the earplug while allowing the structure to be unobtrusive and compact in size while being readily and economically manufacturable.

In accordance with specific features of the invention, a construction is provided which facilitates manufacture and which also permits control of features which enhance acoustical performance, including control of variations in cross-sectional area of the second sound passage along its length. In an illustrated construction, a cap member is mounted on a supporting tube member to provide the second passage folded back on itself, an outer portion of the passage being formed by the space between the inside of the cap member and the tube member in at least partially surrounding relation to an interior portion of the second passage formed by a central opening in the tube member. A small turnaround cavity portion is formed inside the end of the cap member by a cutaway outer tip of the tube member to connect the outer and interior portions of the second passage. In one construction of the invention, the cap and tube members are in generally concentric relation with longitudinally extending spacer ribs or the like being provided on one of the members to provide spaces forming parts of the outer portion of the second passage. In another construction of the invention, the cap member is asymmetrically disposed on the support tube member and is secured thereto, as by cementing or bonding a portion of one side of the outer surface of the support tube to a portion of one side of the inside surface of the cap member.

The structure of the invention which defines the second passage may be used in other ear plug constructions but is particularly desirable for use in an improved audibility earplug of a type as disclosed in the aforesaid Killion U.S. Pat. No. 4,852,683 and further objects of the invention relate to such use of the structure in combination with other features to achieve enhanced performance characteristics.

It is an object of the present invention to provide a more economical earplug exhibiting relatively uniform attenuation throughout the 500 Hz to 6000 Hz frequency range important to speech intelligibility. In particular, it is an object of the present invention to provide an economical earplug whose real ear attenuation at the higher speech frequencies does not appreciably exceed its real ear attenuation at the lower speech frequencies.

Another object of the present invention is to provide an economical earplug exhibiting relatively uniform attenuation throughout most or all of the audible range of frequencies.

Another object of the present invention is to provide a family of earplugs having relatively low, medium, and high average attenuation values, each member of the family exhibiting relatively uniform attenuation throughout most or all of the audible range of frequencies.

It is a further object of the present invention to provide an earplug that uses inexpensive commercially available ready-to-use eartips such as the aforementioned UltraFit eartip or ER3-14 eartip or a shortened version thereof or the like.

It is a further object of the present invention to provide an attenuating assembly that can be readily transferred, without sacrifice in performance, from the aforementioned UltraFit or ER3-14 eartip to a custom earmold, when greater comfort or durability is desired, without requiring the custom earmold to have a precisely tuned internal sound tube.

It is a further object of the present invention to provide an earplug that permits the seal to the ear to occur deeply in the earcanal to reduce or eliminate the occlusion effect and permit the user to experience his own voice in a more natural manner.

It is a still further object of the present invention to provide an earplug that has a distinctive, cosmetically attractive appearance.

These and other objects and features are achieved in the present invention through the use of an earplug construction in which an assembly contains an acoustic damper between two sound channels, the first being the sound tube internal to the eartip and the second being an external tube-plus-cap combination such as aforementioned which forms a "folded horn" construction that has a one-quarter-wavelength resonance at approximately 2700 Hz and is arranged so that its external inlet is placed near the sealed entrance to the earcanal. By suitable choice of a relatively large damping resistance, the resonance between the mass reactance of the internal sound tube and the compliance of the earcanal volume is completely damped, so that the length and diameter of the internal sound tube becomes relatively unimportant.

In the present invention the increased high frequency attenuation resulting from the use of a relatively large damping resistance as described above is partially compensated for by locating the external sound inlet deeply in the concha of the ear, where an increased sound pressure level is produced in the 2 to 10 kHz range of frequencies due to resonances caused by the structure of the concha and the pinna of the ear, as described by E. A. G. Shaw in his chapter "Acoustics of the External Ear" in the book Acoustical Factors Affecting Hearing Aid Performance edited by G. A. Studebaker and I. Hochberg (University Park Press, Baltimore Md, 1980).

A further improvement in high frequency performance is obtained in the present invention by the use of the external "folded horn" configuration in which the effective cross-sectional area of the external sound channel is effectively tapered so that a high-frequency "Horn Effect" is obtained, resulting in an increased transmission of the high frequency sounds. This effect is described in the article "Earmold Options for Wideband Hearing Aids" by M. C. Killion appearing in the Journal of Speech and Hearing Disorders 46, 10-20 (1981).

A still further improvement in high frequency performance is obtained in the present invention by the use of a secondary "small-cavity resonance" formed in the small chamber between the inside of the cap and the outside of the external tube where it connects to the eartip, a resonance which can be tuned to improve the response characteristic in the 4 to 8 kHz frequency region.

By choosing different values of damping resistance and different dimensions for the external sound tube and cap, a family of earplugs is obtained having relatively low, medium, and high average attenuation values, each one of which exhibiting relatively uniform attenuation throughout most or all of the audible range of frequencies.

This invention contemplates other objects, features and advantages which will become more fully apparent from the following detailed description taken in conjunction with the accompanying drawings.

DESCRIPTION OF PREFERRED EMBODIMENTS

Figure 1:
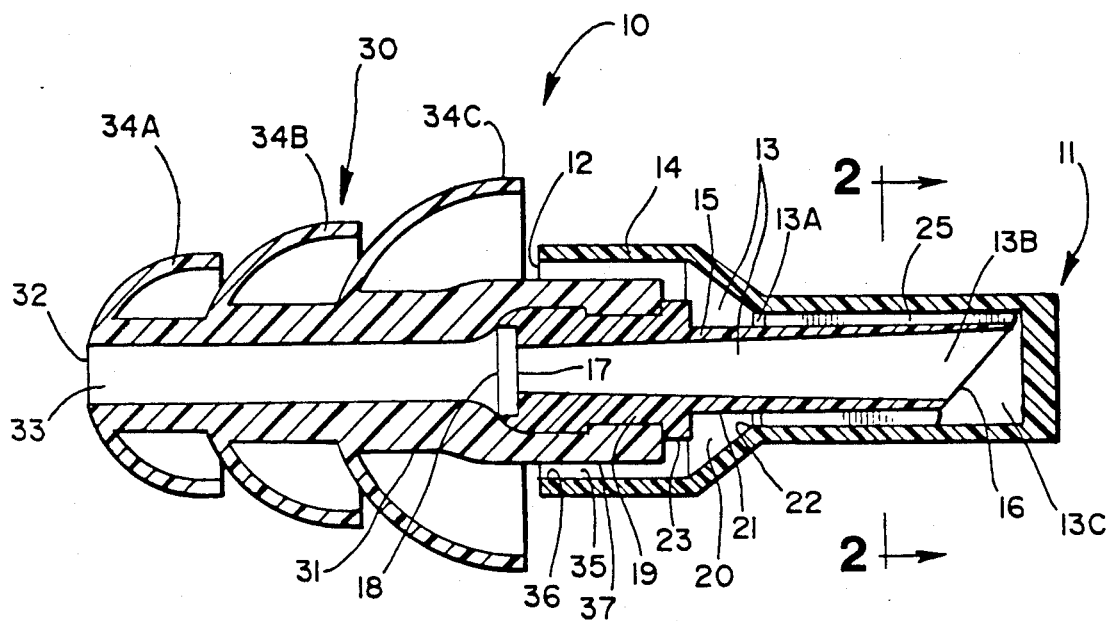
FIG. 1 is a cross-sectional view of the earplug assembly constructed in accordance with the present invention and combined with a triple-flange eartip.
Figure 3:
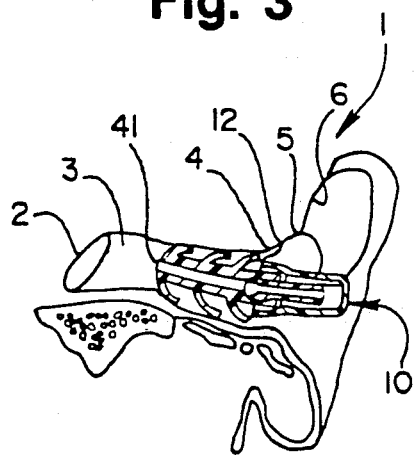
FIG. 3 is a cross-sectional view of the earplug assembly of FIG. 1 properly positioned in an ear.
Figure 5:
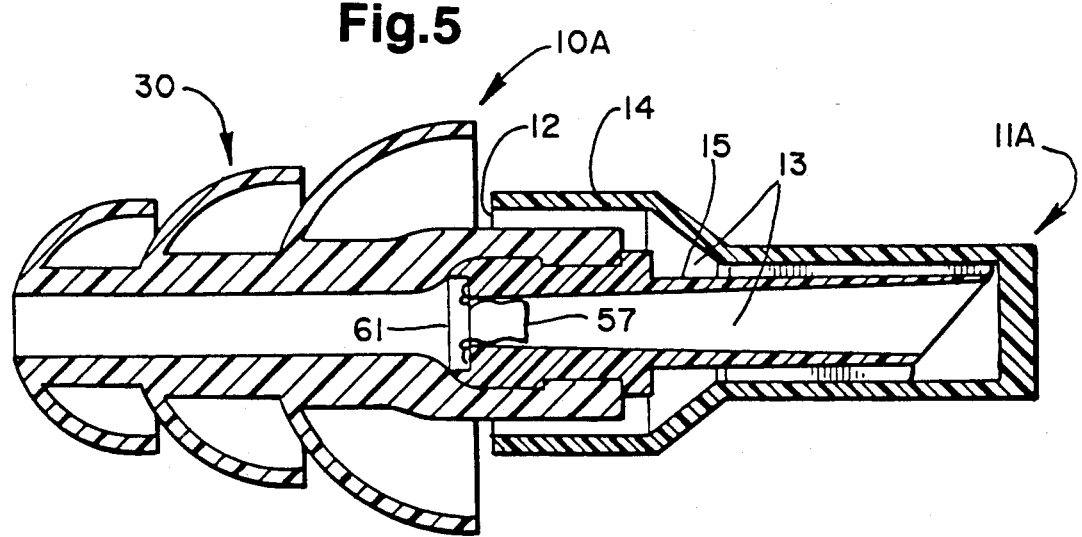
FIG. 5 is a cross-sectional view of another version of the earplug assembly constructed in accordance with the present invention.

The devices of this invention are designed for use with a human ear which is designated by reference numeral 1 in FIG. 3 and which includes an eardrum 2, an ear canal 3 with an entrance 4 thereto, a concha or shell-like structure 5 around the entrance 4 and a pinna or external ear structure 6. One embodiment of an earplug assembly of the invention is shown in FIGS. 1 and 3 and is generally designated by reference numeral 10. Another similar embodiment is shown in FIG. 5 and is generally designated by reference numeral 10A. In both embodiments, an attenuating sub-assembly 11 or 11A is provided which has an external opening 12 and a continuous outer sound channel generally designated by reference numeral 13. Outer sound channel 13 is folded back on itself in what is referred to herein as a "folded horn" configuration in which a portion 13A thereof is formed by the space between a cap 14 and a hollow support tube 15 and is in at least partially surrounding relation to an interior portion 13B formed by the central opening in support tube 15. Portions 13A and 13B communicate with each other at small turnaround cavity portion 13C formed inside the end of cap 14 by the cutaway outer tip 16 of support tube 15. A damping resistance 17 is located at the opposite end of support tube 15 near its internal opening 18. Also in both embodiments, attenuating sub-assembly 11 is adapted to be positioned within the pinna 6 as shown in FIG. 3. The illustrated attenuating subassembly 11 has a general cap-plus-tube configuration. The external opening 12 at one end thereof forms a sound receiving inlet for the earplug 10 and is located within the concha 5 and at a position very close to the entrance 4 of the earcanal 3. The internal opening end 18 of support tube 15 is also positioned within the concha 5, at a position opposite the ear canal entrance 4, to be coupled thereto through eartip subassemblies of different forms which are sealingly attached to support tube 15 at its coupling adapter section 19.

In FIG. 1, a small circumferential cavity 20 is formed between outer surface 21 of support tube 15 and inner surface 22 of cap 14. The volume of air in cavity 20 is partially determined by the dimensions of a locating flange 23 which may preferably be molded around the periphery of hollow support tube 15 at a distance from its internal opening 18 equal to approximately one-third of the total length of hollow support tube 15. Locating flange 23 provides a reliable end stop for the insertion of hollow support tube 15 into tubular extension portion 31 of eartip 30.

Figure 2:
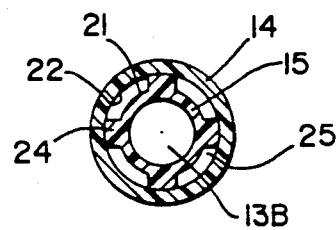
FIG. 2 is a transverse cross-sectional view of the outer tube-plus-cap portion of the earplug assembly of FIG. 1.

FIG. 2 shows a transverse cross-sectional view of section AA through attenuating subassembly 11, illustrating spacer ribs 24 disposed about the perimeter of support tube 15 over a part of its length, support spacer ribs 24 forming a sealing fit to the internal surface 22 of cap 14. Three or four spacer ribs may preferably be used. Along the length of the four spacer ribs 24 illustrated in FIG. 2, surrounding portion 13A of outer sound channel 13 is precisely and reliably defined by its four separate sub portions, one of which is designated by the reference numeral 25 in FIG. 2, said sub portions being formed between ribs 24, internal surface 22 of cap 14, and external surface 21 of support tube 15. Spacer ribs 24 are preferably molded into support tube 15 with the dimensions and materials of the parts such that a push fit is formed between cap 14 and support tube 15. Alternately, spacer ribs 24 may be molded into cap 14 with equivalent results.

Figure 4A:
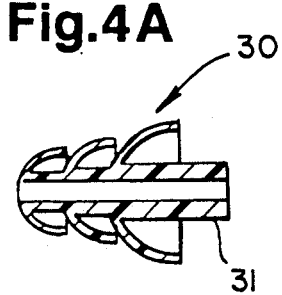
FIG. 4A is a cross-sectional view of the disposable triple-flange eartip that may be employed.

In both FIGS. 1 and 5, and also in FIG. 4A, a premolded eartip 30 is illustrated which has a central opening therethrough and a tubular extension portion 31, an inner outlet end 32 at the opposite end of the central opening from tubular extension portion 31, the complete central opening forming an inner sound channel 33. Eartip 30 is sealed to the ear by means of three flanges 34A, 34B, and 34C. In FIG. 1, the outer end of inner tube portion 31 surrounds the coupling adapter section 19 of support tube 15 and is preferably stretched, as shown, so as to provide an unbroken and nearly uniform diameter sound channel 33 up to the junction between tubular extension portion 31 and coupling adapter section 19. Eartip 30 is preferably molded using a soft polymer suitable for sealing to the earcanal. Flanges 34A, 34B, and 34C of eartip 30 are also preferably molded as reversible flanges for ease in cleaning.

In FIGS. 1 and 5, a more constricted annular sound channel 35 may preferably be formed between inner surface 36 of cap 14 and the stretched outer surface 37 of tubular extension portion 31 of eartip 30. Sound channel 35 leads from external opening 12 to circumferential cavity 20. Sound channel 35 and cavity 20 combine with sub portions 25 to form surrounding portion 13A of outer sound channel 13. Sound channel 35 and cavity 20 may preferably have dimensions chosen for the acoustic contributions of channel 35 and cavity 20, as described more fully below.

Figure 4B:
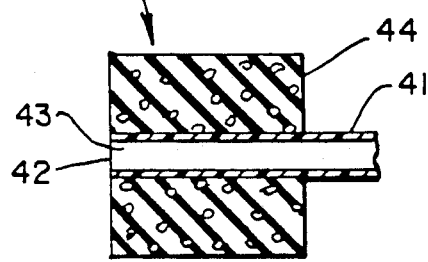
FIG. 4B and FIG. 4C are cross-sectional views of a slow-recovery-foam eartip and a custom earmold assembly, respectively, to illustrate two of the alternate coupling methods possible with the earplug of the present invention.

FIG. 4B illustrates an alternative form of eartip assembly 40, which includes an inner sound tube 41 having an inner outlet end 42 and an inner sound channel 43, a foam eartip 44 being cemented or otherwise secured on the outside of tube 41.

Figure 4C:
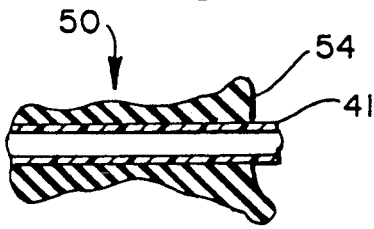

FIG. 4C illustrates another alternative form of eartip assembly 50 in which a custom earmold 54, formed after taking an impression of the ear of a user, is cemented or otherwise secured to the tube 41.

In both of the embodiments of FIGS. 1 and 5, an inner passage of substantially uniform cross-sectional area extends within the tubular extension portion 31 from the inner end 32 of the eartip 30 to the damper 17, whereas the outer passage (generally denoted by numeral 13) between the damper 17 and the sound inlet 12 has a cross-sectional area that varies along its length in a manner empirically determined to provide both a highly desirable "horn effect" and a small-cavity resonance as hereinafter described.

In constructing the device 10, the cap 14 may be formed from polyvinylchloride (PVC) or other moldable polymer, having in the preferred embodiment a total internal length of 0.680 inches and an inside diameter of 0.280 inches starting at external opening 12 and extending back for a distance of 0.214 inches before tapering down at an angle to an inside diameter of 0.149 inches at a distance of 0.302 inches from inlet 12, after which the inside diameter may taper slowly to an inside diameter of 0.142 inches at the maximum distance from inlet 12. Support tube 15 may also be formed from PVC or other polymer, and may have an overall length of 0.748 inches and an inside diameter tapering uniformly from 0.065 inches near damper 17 to 0.076 inches at cutaway outer tip 16. The outer diameter of support tube 15, ignoring spacer ribs 24, may preferably be a nearly uniform 0.110 inches between tip 16 and locating flange 23. Coupling adapter section 19 may preferably have an outer diameter varying between 0.145 inches and 0.179 inches over a length of 0.106 inch measured back from internal opening end 18 of support tube 15, a diameter chosen to stretch and hold tubular extension portion 31 of eartip 30 so that withdrawal of section 19 from tubular portion 31 will be resisted. Spacer ribs 24 are preferably 0.019 inches thick so that a push fit of cap 14 over tube 15 is obtained. Spacer ribs 24 may be 0.030 to 0.050 inches wide. The damping resistance 17 may be formed from dimensionally stable woven filter cloth as described by Carlsen and Mostardo in U.S. Pat. No. 3,950,560 or, alternately, a complete damping assembly such as described by Carlsen and Mostardo and commercially available from Knowles Electronics as the metal barrelled 3300 Ohm BF-1922 damper (or as the fused-mesh-only 3300 Ohm BF-3036 damper) may be substituted for damping resistance 17 by pressing the damper into interior portion 13B of support tube 15 near internal opening end 18. In the case of the BF-1922 damper, a change in the 0.065 inch internal diameter to 0.078 inch internal diameter over the 0.100 inch length of the BF-1922 damper is preferable.

The eartip 30 of FIGS. 1 and 4A may use a premolded three-flange eartip of a type marketed under the trade name "UltraFit" by E-A-R corporation, in which a 0.076 inch hole has been molded down through the center along its axis. In the preferred embodiment, the UltraFit is cut to a total length of 22 mm. With the alternate method of sealing to the ear shown in FIG. 4B, the eartip assembly 40 may use a plug of foam plastic, of a type marketed under the trade name "E-A-R", in which a hole has been formed to accept the inner sound tube 41 which may typically be formed from #13 vinyl tubing having an inside diameter of 0.076 inches and an outside diameter of 0.109 inches. With this construction, the eartip assembly is a shortened version of an Etymotic Research ER3-14 eartip, with a resulting total length of 22 mm for inner sound tube 41 before it is stretched over adapter section 19. With the alternate method of sealing to the ear shown in FIG. 4C, the earmold assembly 50 is obtained by taking an impression of the ear and sending it to a hearing aid earmold laboratory in the customary manner to obtain the custom earmold 54 with the tubing 41 being unbent #13 vinyl tubing, tubing 41 being cemented in place. It will be understood that any method of sealing to the ear may be used which includes an inner sound channel equivalent to a section of #13 tubing.

FIG. 3 illustrates the proper location of the complete earplug assembly 10 of FIG. 1 in the earcanal 3 of the illustrated ear 1, applicable also to the assembly 10A of FIG. 5. The sound inlet 12 of the attenuating subassembly 11 is located as close as possible to the entrance 4 of the earcanal so that the increased sound pressure level or "SPL" developed by resonances in the cavities formed by the concha 5 and the pinna 6 will be made available at sound inlet 12. Note that because of the overlap of cap 14 and support tube 15 the physical length of complete sound channel 13 is approximately 32 mm between external opening 12 and damping resistance 17, taking the shortest path around cutaway, tip 16. Because of the circumferential nature of external opening 12, the "end effect" introduced by the reactive component of the radiation impedance seen looking out from the opening 12 is relatively small, so that the effective acoustical length of the sound channel is nearly equal to its physical length of 32 mm, and so that a quarter-wave resonance boost is obtained at approximately 2700 Hz (frequency in kHz=one-fourth the velocity of sound in thousands of mm per second divided by the length in mm=86/32=2.687 kHz). Similarly, the gradually increasing cross-sectional area of tapered sound channel 13B in support tube 15 and the increasing cross-sectional area of sound channel 13A as it approaches opening 12 provides a broadband increase in sound pressure level above about 3 kHz due to "horn action" acting to improve the coupling between the relatively low acoustic source impedance presented by the free air in the vicinity of the earcanal entrance 4 and the relatively high acoustic load impedance presented by the air in the earcanal 3. Both the quarter-wave and horn-action phenomena are reviewed in the appendix of my aforementioned article "Earmold options for wideband hearing aids," the disclosure thereof being incorporated herein by reference.

During experiments with prototypes of the new tube-plus-cap construction, it was discovered that the cap provided an important additional benefit in that it readily provides an additional high-frequency response-control measure because of the presence of a secondary resonance formed in the small circumferential cavity 20 between the inner surface 22 of the cap 14 and the outer surface 21 of the support tube 15, a resonance whose frequency can be adjusted to improve the response characteristic in the 4 to 8 kHz frequency region by changing the volume of the cavity and/or the acoustic mass of annular sound channel 35. Indeed, it was discovered that an undesirably large increase in SPL delivered to the ear (decrease in attenuation) can be obtained at resonance if insufficient damping is available. By adjusting the dimensions of annular sound channel 35, in particular the spacing between inner surface 36 of cap 14 and outer surface 36 of tubular extension portion 31 of eartip 30, an appropriate amount of damping may be introduced so that a well-controlled resonance boost is obtained as illustrated below. To explain further: In an annular sound channel, the acoustic resistance varies as the inverse cube of the spacing distance, whereas the acoustic mass varies inversely as the first power of the spacing distance, and both vary in direct proportion to the acoustic length (which in the case of annular sound channel 35 is the distance between sound inlet 12 and cavity 20), a relatively independent control of acoustic mass and acoustic resistance is available so that both the frequency and amplitude of the resonance boost may be adjusted.

FIG. 5 shows a complete earplug assembly 10A wherein a damper assembly 57 is sealingly disposed in and near the end 18 of sound channel 13B of support tube 15 of attenuating subassembly 11A. Damper assembly 57 may be a 3300 Ohm Knowles BF-1922 damping plug as described above. A flexible diaphragm 61 is also sealingly disposed in and near the internal opening 18 of sound channel 13B of support tube 15 of attenuating subassembly 11A. Flexible diaphragm 61 is added as a series acoustic compliance element to provide increased attenuation at very low frequencies. The operation is the same as the operation obtained with a diaphragm in the aforementioned Killion earplug in that it serves only to increase attenuation at low frequencies, and differs only in its use in an earplug which contains an additional small-cavity resonance. Diaphragm 61 has no practical influence on the magnitude or frequency of the small-cavity resonance because in the practical case its reactance will be small compared to the resistance of damping element 60 in the 4 to 8 kHz region.

Figure 6:
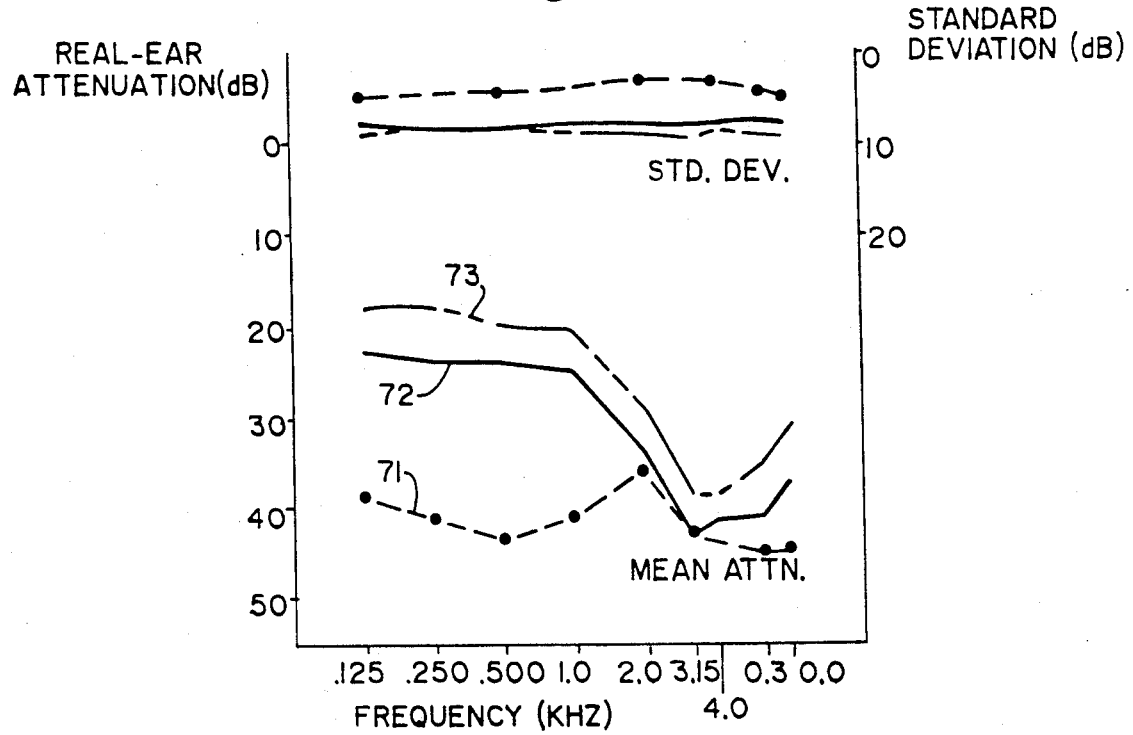
FIG. 6 shows the real ear attenuation frequency response curves of various earplug configurations for illustration of the problems inherent in present low-cost earplugs.

FIG. 6 is a graph in which data on the average real-ear attenuation of the widely used E-A-R foam earplug is shown as measured under laboratory and field conditions and reported by Elliott Berger in a Letter-to-the-Editor appearing on pages 88-90 of Noise Control Engineering Journal May-June 1987. Curve 71 shows the attenuation which can be obtained under laboratory conditions with deeply inserted earplugs, typically 40 dB. The problem is that 40 dB of attenuation, when added to the mild "internal attenuation" inflicted by the mild hearing loss of, for example, a typical 50 year old male, will make it difficult or impossible for him to understand conversational speech or hear the operation of his machinery. When the E-A-R plug is only partially inserted, however, an attenuation of only approximately 20 dB is obtained at low frequencies, making it possible for him to hear at least the low-frequency portions of speech and machinery sounds. Two extensive studies at DuPont, a company committed to hearing conservation and where hearing protection is mandatory in noisy areas, have resulted in the "real-world" attenuation data shown in curves 72 and 73, respectively. One possible explanation for at least some of the difference between laboratory and real-world data is that the workers intentionally insert their earplugs only partially in order to hear better. The problem with this "partial insertion solution" is that important high-frequency speech cues and machinery "clicks" will be only slightly more audible than before, as illustrated by the nearly-equal attenuation shown in the 2 to 6.3 kHz frequency range for curves 71, 72, and 73.

Figure 7:
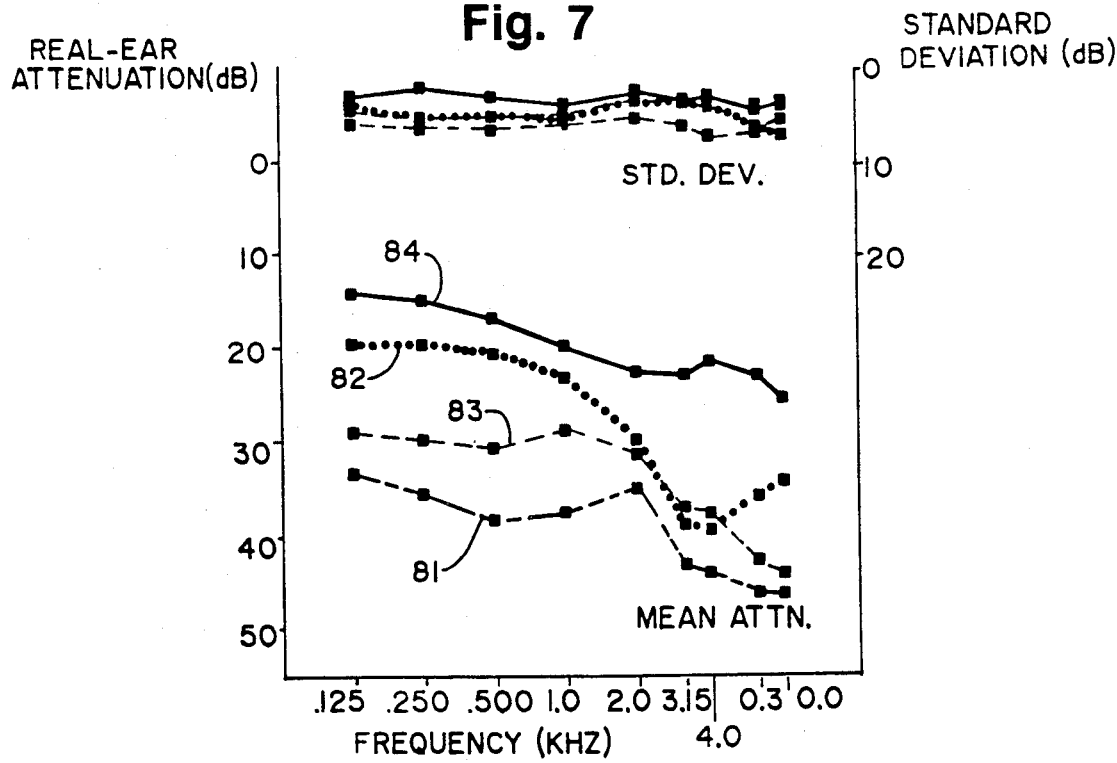
FIG. 7 shows the real ear attenuation frequency response curves of various earplugs for illustration of the improved high frequency characteristics of the earplugs of the invention compared to existing low-cost earplugs.

FIG. 7 is a graph in which the laboratory-measured real-ear attenuation of three earplugs is shown plotted verses frequency. Curve 81 shows the attenuation of the E-A-R foam earplug measured with "standard insertion," somewhat less than deep insertion. Curve 82 shows the attenuation of the E-A-R foam earplug measured with partial insertion. Note that the attenuation shown in curve 82 is quite similar to that shown in curves 72 and 73 of FIG. 6, supporting Berger's hypothesis that the real-world data reflected partially inserted earplugs. Curve 83 shows the attenuation of the aforementioned three-flange molded UltraFit earplug with standard insertion. Again, note that all of the earplug attenuation data shown in curves 81, 82, and 83 provide excessive attenuation for the three-fourths of the aforementioned noise exposed workers who need only 10 dB or less of attenuation in order to have adequate hearing protection. Finally, curve 84 shows the much improved (reduced) attenuation, particularly at the higher frequencies, provided by earplugs of the invention. The data plotted in curve 84 were obtained on 10 subjects in the same E-A-R diffuse-field facilities as the data for curves 81, 82, and 83, and thus are directly comparable.

Figure 8:
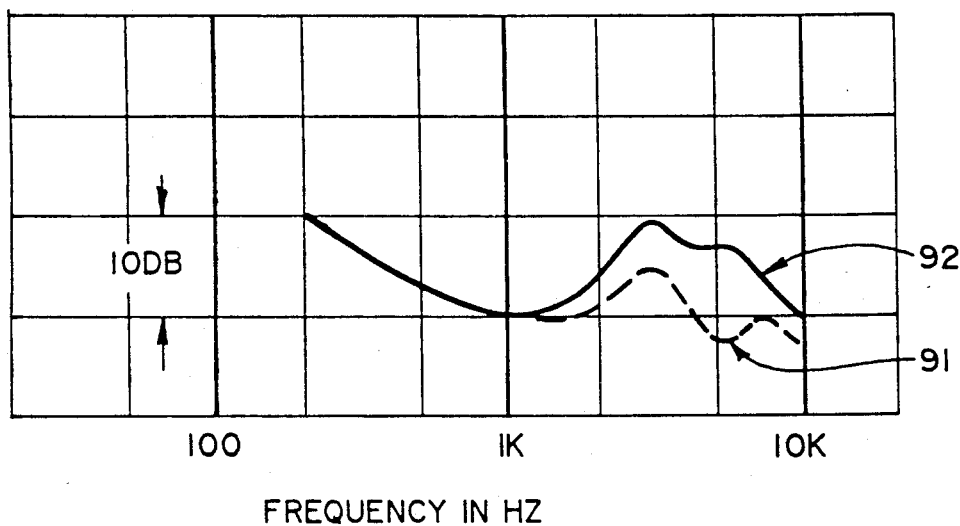
FIG. 8 is a graph showing and comparing the frequency response characteristics obtainable with the Killion loop-tube earplugs adjusted to provide approximately 20 dB of real-ear attenuation at 1 KHz, and with the earplugs of the invention.

FIG. 8 is a graph showing measurements of the estimated relative sound pressure level at the eardrum versus frequency, similar to FIG. 8, of the aforementioned Killion patent, showing the frequency response characteristics of two earplug constructions as measured on an ear simulator. Curve 91 shows the average response measured on samples of the Killion loop-tube earplug construction. Curve 92 shows the improved high-frequency response (greater transmission of sound to the eardrum and thus reduced attenuation) obtained from the improved horn action and properly adjusted small-cavity resonance in the earplugs of the invention.

Figure 9A:
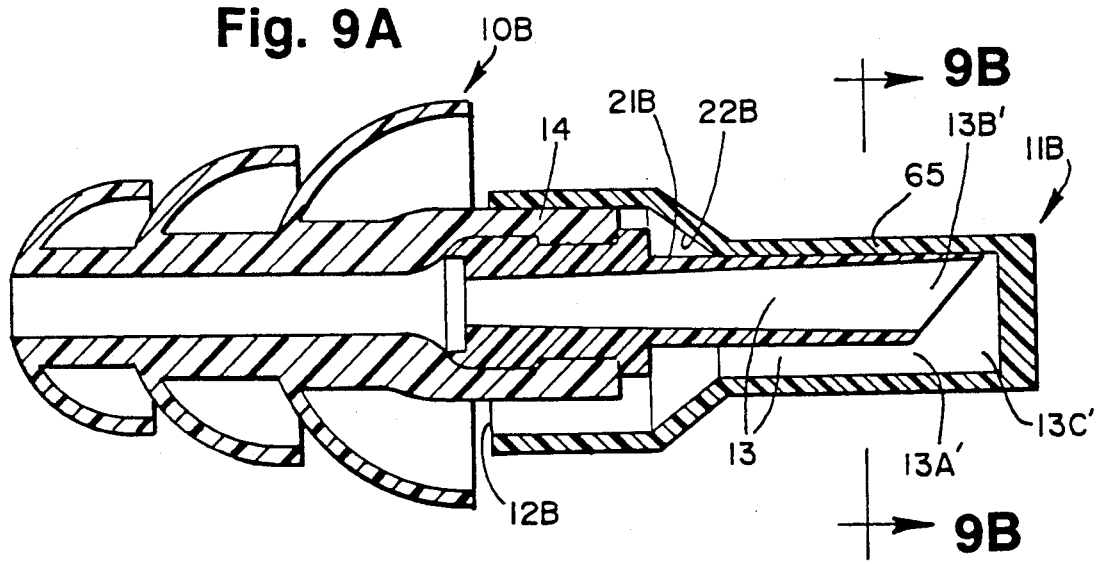
FIG. 9A is a cross-sectional view of still another version of the earplug assembly constructed in accordance with the present invention.
Figure 9B:
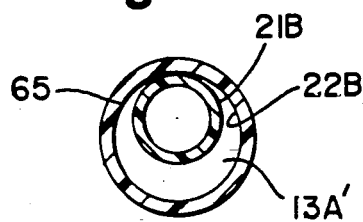
FIG. 9B is a transverse cross-sectional view of the outer tube-plus-cap portion of the earplug of FIG. 9A.

FIG. 9A shows a modified attenuating subassembly 11B in which cap 14 is asymmetrically disposed on exterior support tube 15B. Support tube 15B is molded without spacer ribs so that a smooth surface 21B mates to smooth surface 22B of cap 14 providing surfaces suitable for solvent bonding at bond or cement line 65. Outer sound channel 13 in FIG. 9A is similar in operation to outer sound channel 13 in FIG. 1, but surrounding portion 13A' has a semi-annular configuration that somewhat resembles a quarter-moon in its cross-sectional view. FIG. 9B shows the transverse cross-sectional view through section A-A of FIG. 9A, and better illustrates the semi-annular configuration of surrounding portion 13A'. In a similar fashion, external sound receiving inlet opening 12B has a semi-annular configuration also resembling a quarter-moon in its cross-sectional view (not shown). Prototype production samples of the configuration generally denoted as 10B have been assembled and tested, providing measured attenuation characteristics comparable to those of the construction shown in FIG. 1.

It should be noted that even the improved high frequency characteristic shown in curve 84 of FIG. 7 represents more attenuation than required for many workers, but it was intentionally chosen as a compromise in order to provide a Noise Reduction Rating of approximately 12 dB so that even with normal production variations a minimum NRR of 10 dB can be expected. Because the attenuation characteristics of the earplugs of the present invention may be adjusted over a fairly wide range while still maintaining a relatively uniform attenuation with frequency, a family of such earplugs is under development, each member having a different average attenuation. It will be readily understood that such a family falls within the teachings of this disclosure, and is in accordance with the principles explained herein.

It will be understood that other modifications and variations may be effected without departing from the spirit and scope of the novel concepts of this invention.

We claim:

1. An earplug, comprising: first passage means arranged for positioning with at least an inner end portion thereof in an earcanal to define a first sound passage extending from an inner end within the ear canal to an opposite outer end, and second passage means defining a second sound passage having an inner end coupled to said outer end of said first passage and having an opposite sound-receiving outer end, said second passage including a portion folded back on itself and being operative to enhance the acoustical response characteristics of the earplug while allowing said second passage means to be unobtrusive and compact in size, said sound-receiving outer end of said second sound passage being arranged as an annular opening around said inner end of said second sound passage.

2. An earplug comprising: first passage means arranged for positioning with at least an inner end portion thereof in an earcanal to define a first sound passage extending from an inner end within the ear canal to an opposite outer end, and second passage means defining a second sound passage having an inner end coupled to said outer end of said first passage and having an opposite sound-receiving outer end, said second passage including a portion folded back on itself and being operative to enhance the acoustical response characteristics of the earplug while allowing said second passage means to be unobtrusive and compact in size, said sound-receiving outer end of said second passage being arranged as semi-annular opening around said inner end of said second passage.

3. An earplug as defined in claim 1, further including a relatively large acoustic resistance means arranged for cooperation with an intrinsic acoustic mass reactance of said first passage and an intrinsic acoustic compliance of the ear canal to provide a substantially non-resonant acoustic compliance, said second passage having a length of approximately one-fourth wavelength at a frequency at which the response of the ear is at a maximum.

4. An earplug as defined in claim 1, said outer end of said second passage forming a sound inlet for said earplug and being positioned in proximity to an entrance to the earcanal.

5. An earplug as defined in claim 1, said first passage means comprising a central opening in a premolded flexible flanged eartip.

6. An earplug as defined in claim 5, said premolded flexible flanged eartip having a tubular extension portion.

7. An earplug as defined in claim 1, said first passage means comprising a generally straight tube, and a compressible foam member surrounding said tube.

8. An earplug as defined in claim 5, said central opening in said flanged eartip having a diameter which is a small fraction of an inside diameter of an earcanal.

9. An earplug as defined in claim 7, said tube having an outside diameter which is a small fraction of an inside diameter of the earcanal.

10. An earplug as defined in claim 1, wherein said second passage provides a horn effect.

11. An earplug as defined in claim 10 wherein said first passage is of uniform cross-sectional size and said second passage has a cross-sectional size generally increasing between said coupling with said first passage and said sound receiving outer end in order to obtain said horn effect.

12. An earplug as defined in claim 1, wherein said second passage includes portions which provide a secondary resonance operative to obtain a high-frequency resonance boost by said earplug.

13. An earplug as defined in claim 3, said acoustic resistance means comprising foraminous means positioned in proximity to said outer end of said first passage.

14. An earplug as defined in claim 13, further including acoustic compliance means in series relation to said first and second passages and operative to increase attenuation in a lower portion of the audible spectrum.

15. An earplug as defined in claim 14, said acoustic compliance means comprising a diaphragm positioned in proximity to said acoustic resistance means.

16. A compact and unobtrusive earplug structure for forming a sound passage folded back on itself to obtain enhanced acoustical characteristics, said structure comprising: a hollow support member providing an internal passage forming a first part of said sound passage, a cap member mounted on said hollow support member and including an end wall portion and an axially extending wall portion having an inner surface portion in spaced relation to an outer surface portion of said hollow support member to define a second part of said sound passage, an inside surface portion of said end wall portion of said cap member and an end surface portion of said hollow support member being in spaced relation to provide communication between said first and second parts of said sound passage.

17. A structure as defined in claim 16, including axially extending rib means on one of said members for engaging the other during assembly and for providing said spaced relation between said inner surface of said axially extending wall portion of said cap member and said outer surface of said hollow support member.

18. A structure as defined in claim 16, wherein the relative dimensions of sound passage-defining surfaces of said support and cap members are such as to obtain changes in cross-sectional area of said sound passage along the length thereof and to provide predetermined acoustical characteristics.

19. A structure as defined in claim 18, wherein said changes in cross-sectional area of said sound passage are such as to obtain a horn operation.

20. An earplug, comprising: first passage means arranged for positioning with at least an inner end portion thereof in an earcanal to define a first sound passage extending from an inner end within the ear canal to an opposite outer end, and second passage means defining a second sound passage having an inner end coupled to said outer end of said first passage and having an opposite sound-receiving outer end, said second passage including a portion folded back on itself and being operative to enhance the acoustical response characteristics of the earplug while allowing said second passage means to be unobtrusive and compact in size, wherein said second passage provides a horn effect, and wherein said first passage is of uniform cross-sectional size and said second passage has a cross-sectional size generally increasing between said coupling with said first passage and said sound receiving outer end in order to obtain said horn effect.

21. An earplug, comprising: first passage means arranged for positioning with at least an inner end portion thereof in an earcanal to define a first sound passage extending from an inner end within the ear canal to an opposite outer end, and second passage means defining a second sound passage having an inner end coupled to said outer end of said first passage and having an opposite sound-receiving outer end, said second passage including a portion folded back on itself and being operative to provide a primary resonance effect to enhance the acoustical response characteristics of the earplug while allowing said second passage means to be unobtrusive and compact in size, wherein said folded back portion of said second passage includes surfaces which define a small cavity having a greater cross sectional area which is operative to provide a secondary resonance and to obtain a high-frequency resonance boost in a 4-8 KHZ range.

* * * * *